United States Patent
Greiser

(10) Patent No.: US 9,354,290 B2
(45) Date of Patent: May 31, 2016

(54) METHOD AND MAGNETIC RESONANCE SYSTEM TO GENERATE AN MR IMAGE WITH A TRACKING FACTOR

(75) Inventor: Andreas Greiser, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 1096 days.

(21) Appl. No.: 13/410,632

(22) Filed: Mar. 2, 2012

(65) Prior Publication Data
US 2013/0060126 A1 Mar. 7, 2013

(30) Foreign Application Priority Data

Mar. 3, 2011 (DE) .......................... 10 2011 005 046

(51) Int. Cl.
| | |
|---|---|
| A61B 5/00 | (2006.01) |
| G01R 33/567 | (2006.01) |
| A61B 5/055 | (2006.01) |
| G01R 33/563 | (2006.01) |

(52) U.S. Cl.
CPC ............ *G01R 33/5676* (2013.01); *A61B 5/055* (2013.01); *A61B 5/7289* (2013.01); *A61B 2576/023* (2013.01); *G01R 33/5635* (2013.01)

(58) Field of Classification Search
CPC ............. A61B 2576/023; A61B 5/055; A61B 5/7289; G01R 33/5635; G01R 33/5676
See application file for complete search history.

(56) References Cited

U.S. PATENT DOCUMENTS

| | | | |
|---|---|---|---|
| 2002/0026115 A1 | 2/2002 | Nehrke et al. | |
| 2005/0074154 A1* | 4/2005 | Georgescu ................ | G06T 7/20 382/128 |
| 2006/0183999 A1 | 8/2006 | Lorenz et al. | |
| 2007/0244386 A1 | 10/2007 | Steckner et al. | |
| 2008/0205730 A1 | 8/2008 | Stehning et al. | |
| 2009/0278539 A1* | 11/2009 | Beatty ........................... | 324/312 |

OTHER PUBLICATIONS

"A Fully Automatic and Highly Efficient Navigator Gating Technique for High-Resolution Free-Breathing Acquisitions: Continuously Adaptive Windowing Strategy," Jhooti et al., Magnetic Resonance in Medicine, vol. 64 (2010) pp. 1015-1026.

* cited by examiner

*Primary Examiner* — Amanda Lauritzen Moher
(74) *Attorney, Agent, or Firm* — Schiff Hardin LLP

(57) ABSTRACT

For the generation of a magnetic resonance (MR) image of a predetermined volume segment of a living subject, a tracking factor is determined for each of different regions of the volume segment, from which the position of the respective region can be determined depending on a position of a moving area of the subject. MR image data of the volume segment are acquired for different positions of the moving area. The position of the moving area is calculated depending on the position and the tracking factor of the respective region, and the MR image data of the respective region are reconstructed using the MR image data of the volume segment corresponding to the calculated position of the moving area. The MR image of the predetermined volume segment is generated as a combination of the constructed MR image data of the regions.

12 Claims, 3 Drawing Sheets

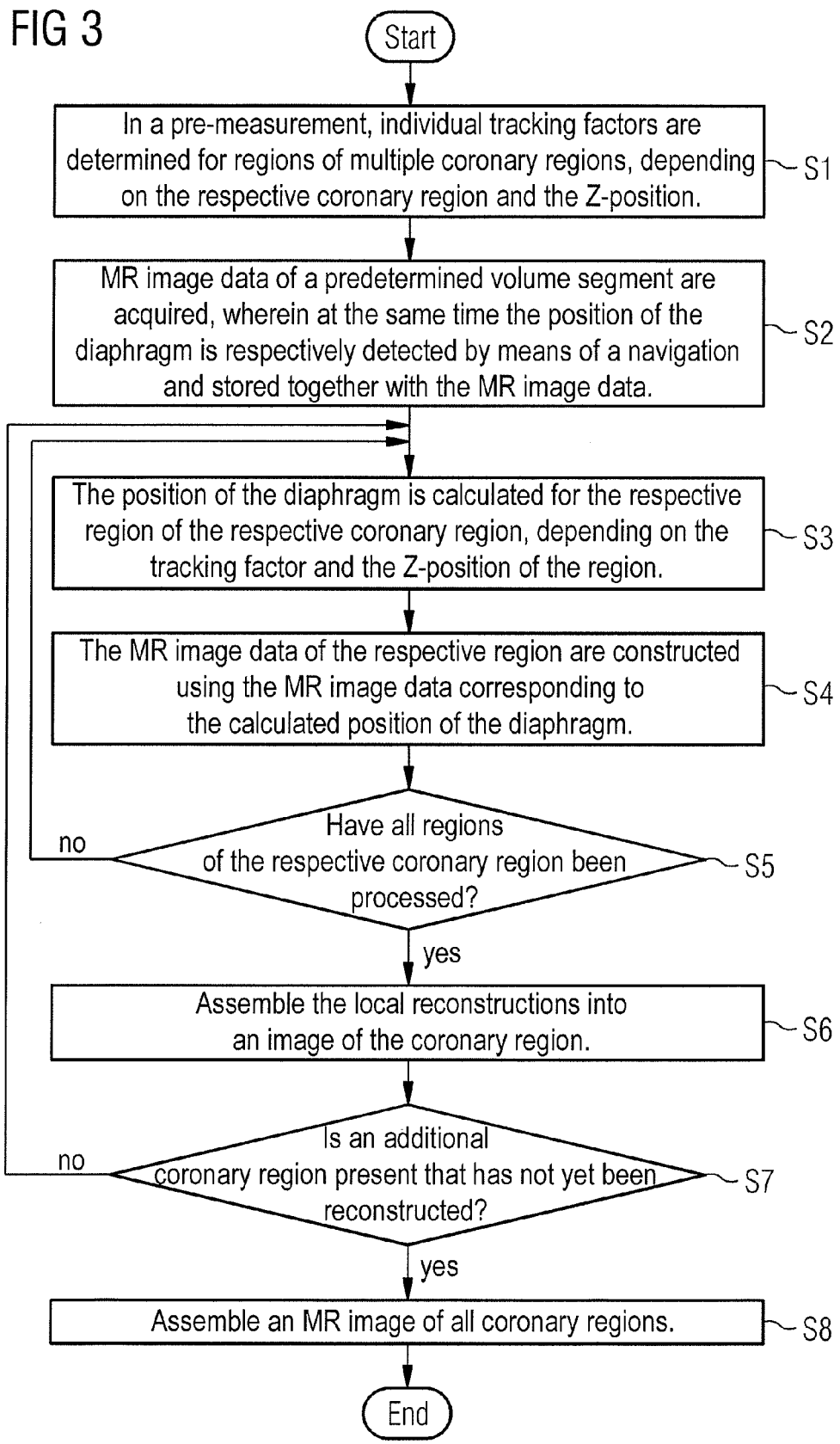

METHOD AND MAGNETIC RESONANCE SYSTEM TO GENERATE AN MR IMAGE WITH A TRACKING FACTOR

BACKGROUND OF THE INVENTION

1. Field of the Invention

The invention concerns a method and a magnetic resonance (MR) system to generate MR images with a tracking factor that indicates a linear correlation between a diaphragm position and a heart position (or between a diaphragm displacement and a heart displacement in a patient).

2. Description of the Prior Art

According to the prior art, for image reconstruction the MR data are acquired with gating in MR coronary imaging. This means that MR data that are measured (acquired) outside of a pre-established acceptance window for the diaphragm position are discarded and measured again until the data acquisition has occurred within the predetermined acceptance window.

According to a more recent method ("A Fully Automatic and Highly Efficient Navigator Gating Technique for High-Resolution Free-Breathing Acquisitions: Continuously Adaptive Windowing Strategy", P. Jhooti et al., Magnetic Resonance in Medicine, 2010), the MR data are collected until the MR data have been acquired sufficiently for an arbitrary breathing position. A reconstruction for this breathing position subsequently occurs using these MR data. MR data that are not required for reconstruction are discarded.

SUMMARY OF THE INVENTION

An object of the present invention is to generate MR images with the use of an adaptive tracking factor, with the MR images generated in such a manner having a higher quality than is typical according to the prior art.

The above object is achieved in accordance with the present invention by a method to generate an MR image of a predetermined volume segment of a living examination subject by operating a magnetic resonance system that includes the following steps:

For multiple regions of the volume segment, respective corresponding tracking factors are determined so that each region has its individual tracking factor. Depending on the position of a moving area (the diaphragm, for example) of the examination subject, the position of the respective region can be determined by the corresponding tracking factor (of this region). In other words, according to the invention it is not only one tracking factor that is used but rather multiple tracking factors, with each region having at least one individual tracking factor associated therewith. For example, these tracking factors can be determined in a pre-measurement by the position of the moving area and the positions of the corresponding regions being determined in this pre-measurement, and then the tracking factors are calculated from this position information. Each tracking factor indicates a linear correlation between the position of a moving area and the position of the respective area for which the respective tracking factor was determined or for which the respective tracking factor applies (or between the displacement of the moving area and the displacement of the respective region). With an individual tracking factor of the respective region that is determined in this step, either the position of the respective region can be determined based on the position of the moving area, or the position of the moving area can be determined with the tracking factor based on the position of the respective area.

MR image data of the volume segment are acquired for different positions of the moving area. In other words: given each acquisition of MR image data of the volume segment, the position of the moving area is detected so that the position of this moving area at which the MR image data have been acquired is respectively known for the acquired MR image data.

In the reconstruction of an MR for one of the regions, the following steps are implemented.

Depending on the position of the respective region, the corresponding position of the moving area is calculated with the use of the tracking factor of the respective region. In other words, according to the invention the calculation of the position of the moving area takes place based on the position of the respective region by means of the tracking factor, which is the reverse of the prior art. The position of the respective region can be registered, for example, by the determination of the position of a prominent point of the respective region (the heart, for example).

For the position of the moving area that is calculated in such a manner, the MR image data of the volume segment that were previously acquired for this position of the moving area are determined (for example are read out from a corresponding memory), or the MR image data for the calculated position are generated (reconstructed) from other acquired MR. These determined or generated MR image data are then used for construction or reconstruction of the MR image data of the respective region. The MR data that are determined for a defined position of the moving area are thus assigned to a defined (new or different) position within the volume segment, depending on the tracking factor.

The MR image data of the various regions that are constructed in such a manner are combined in order to generate the MR image of the predetermined volume segment.

Since, in contrast to the prior art, multiple tracking factors are used, wherein each region of the volume segment has a tracking factor that matches it precisely, the MR image reconstructed for the volume segment can be generated with a higher quality. According to the invention, in the presentation of the human heart (for example) the multiplicity of MR coronary data with regard to the breathing position is utilized such that the MR image data are reconstructed for different tracking factors.

By virtue of various MR image data that have respectively been reconstructed with a locally optimal tracking factor being combined into a combined image, the presentation of coronary arteries (for example) by means of MR imaging can be improved due to reduced breathing artifacts.

The present invention enables MR data acquired outside of an acceptance window known according to the prior art to also be utilized in order to reconstruct MR image data for additional positions of the moving area (for example breathing positions).

As noted above in the description of the advantages according to the invention, in a preferred embodiment the examination subject is a mammal and the moving area is a diaphragm of this mammal and/or the predetermined volume segment is at least one partial area of the heart of the mammal, and this partial area may encompass the immediate environment of the heart. According to this embodiment, the predetermined volume segment can encompass the entire heart with or without the immediate environment of the heart. The "environment of the heart" means the region that surrounds the heart, but lies outside of the heart.

For example, the predetermined volume segment can be the coronary area (i.e. in particular the coronary vessels) of a mammal, namely a human. Each coronary region can correspond to a region for which an individual tracking factor is then determined. It is also possible for each coronary region to be subdivided into multiple regions, with an individual tracking factor being determined for each of these multiple regions.

For example, the regions of the volume segment can be arranged atop one another or one after another in the Z-direction (i.e. in the direction of the basic magnetic field of the magnetic resonance system) so that the positions of these regions arranged one after another in the Z-direction but respectively differing in their Z-coordinates.

In other words, in the aforementioned example the tracking factor is dependent on the Z-position. According to the invention, the tracking factor is therefore dependent on the following influencing variables:

on the examination subject, in particular on the person to be examined, or better on the individual anatomy of the patient.

on a volume sub-segment of the volume segment in which the respective region is located. For example, the volume sub-segment can be a specific coronary branch (a specific coronary vessel), such that the respective tracking factor can be specific to individual coronary branches.

on a Z-position within the corresponding volume sub-segment.

In summary, according to the example described in the preceding the tracking factor is dependent on the specifically considered position in the heart, such that the tracking factor must be determined in the pre-measurement for each of these positions. The correction based on the tracking factor is thereby more precise than according to the prior art, and as a result leads to no remaining movement blurring in the coronary presentation.

It is noted that, according to the invention, the tracking factor can also be dependent on the X-position and/or the Y-position (on the axes perpendicular to the Z-direction) within the corresponding volume sub-segment, in addition to being dependent on the Z-position within said corresponding volume sub-segment. For example, this is the case when a coronary artery runs at the rear wall of the heart and there different tracking factors are measured in the pre-measurement for different X-positions and/or Y-positions.

According to preferred embodiment according to the invention, the MR image data of the volume segment are acquired in steps. In each of these steps, only MR data of a partial segment of k-space (and not the entirety of data of k-space) are acquired. The entirety of k-space corresponds to the predetermined volume segment, or more specifically to a volume that represents or encompasses the predetermined volume segment, independent of the position of the moving area (and therefore independent of the movement of the regions of the volume segment that are to be acquired). Since the moving area (if it is the diaphragm, for example) moves continuously and thus changes its position, in this embodiment the different partial segments of k-space are acquired for different positions of the moving area. Expressed differently, all partial segments of k-space have in fact been acquired after a complete acquisition of k-space, with each partial segment having been acquired at a different position of the moving area. Naturally, it is possible that two or more partial segments may have been acquired (by random coincidence) at the same position of the moving area.

After a repeated scanning of k-space, each partial segment of k-space has accordingly been acquired repeatedly at (normally) different positions of the moving area. Nevertheless, according to the invention the case can occur that a specific partial segment for the position of the moving area that is calculated from the position of the respective region and the corresponding tracking factor is not present in the reconstruction of the MR image data of the respective region (since the partial segment has not been acquired for this position of the routing area in the acquisition of the data from k-space). In this case, according to the invention the following possibilities exist:

Instead of the MR data of the partial segment for the sought position of the moving area, MR data are used which have likewise been acquired for this partial segment but not for the sought position of the moving area, but rather have been acquired for a position of the moving area which lies as close as possible to the sought position.

With the use of the method of compressed scanning ("compressed sensing"), MR data for each combination of partial segment and position of the moving area are constructed from the MR data acquired in k-space without each partial segment having been scanned at every possible or predetermined position of the moving area. The method of compressed sensing means or designates a method by means of which relatively good results for points for which scanning values or measurement values are at least partially absent can be reconstructed, even based on scanning methods or measurement methods that do not scan or measure with high density (but rather with gaps or sparsely).

However, according to the invention it is also possible for the predetermined positions of the moving area to be determined (for example from predetermined positions along the Z-axis, for example at every full millimeter of the z-position), and that MR data of the partial segments of k-space are acquired until MR data have been acquired for each combination of a partial segment and a predetermined position.

In this case, it is ensured that the MR data of all partial segments are also present in the reconstruction of the MR image for an arbitrary region for the sought position of the moving area.

The present invention also encompasses a magnetic resonance system for the acquisition of MR image data. The magnetic resonance system has a basic field magnet, a gradient field system, an RF antenna, and a control device in order to control the gradient field system and the RF antenna, to receive measurement signals received by the RF antenna, to evaluate these measurement signals and thus to acquire MR image data. Moreover, the magnetic resonance system has a navigator in order to determine the position of a moving area (in particular the diaphragm) during the acquisition of the measurement signals or MR image data. The magnetic resonance system is able to determine respective tracking factors for different regions of the volume segment. Moreover, the magnetic resonance system is designed such that MR image data of the volume segment can be acquired for different positions of the moving area, so the respective position of the moving area can be determined in the acquisition of the MR image data. For the region of the MR image for the respective region, a processor of the magnetic resonance system implements the following steps:

The processor determines the position of the moving area depending on the position of the respective region and the tracking factor which has been determined for this region.

The processor reconstructs the MR image data of the respective region using those MR image data of the volume segment that have been acquired for the previously calculated position of the moving area.

The processor magnetic resonance system reconstructs the MR image of the predetermined volume segment in that said magnetic resonance system combines the reconstructed MR image data of the regions.

The advantages of the magnetic resonance system according to the invention essentially correspond to the advantages of the method according to the invention described above.

The above object also is achieved in accordance with the present invention by a non-transitory, computer-readable data storage medium encoded with programming instructions that, when the storage medium is loaded into a computerized control and evaluation system of a magnetic resonance imaging system, cause the control and evaluation system to operate the magnetic resonance system according to any or all of the above-described embodiments.

The software (programming instructions) can be source code (C++, for example) that must still be compiled (translated) and linked or that only must be interpreted, or it can be an executable software code that has only to be loaded into the corresponding computer for execution.

The electronically readable data medium can be a DVD, a magnetic tape or a USB stick, for example on which is stored electronically readable control information, in particular software (see above).

The present invention achieves sharper (in comparison to the prior art) coronary imaging under consideration of the heart displacement due to breathing movements. Naturally, the present invention is not limited to this preferred field of application since, in principle, the present invention can be used in any situation in which a fixed (for example linear) correlation is present between the movement of a moving area and the movement of a volume segment that should be graphically acquired during the movement.

BRIEF DESCRIPTION OF THE DRAWINGS

FIG. 3 is a flow chart of an exemplary embodiment of the method according to the invention.

DESCRIPTION OF THE PREFERRED EMBODIMENTS

Figure 1:
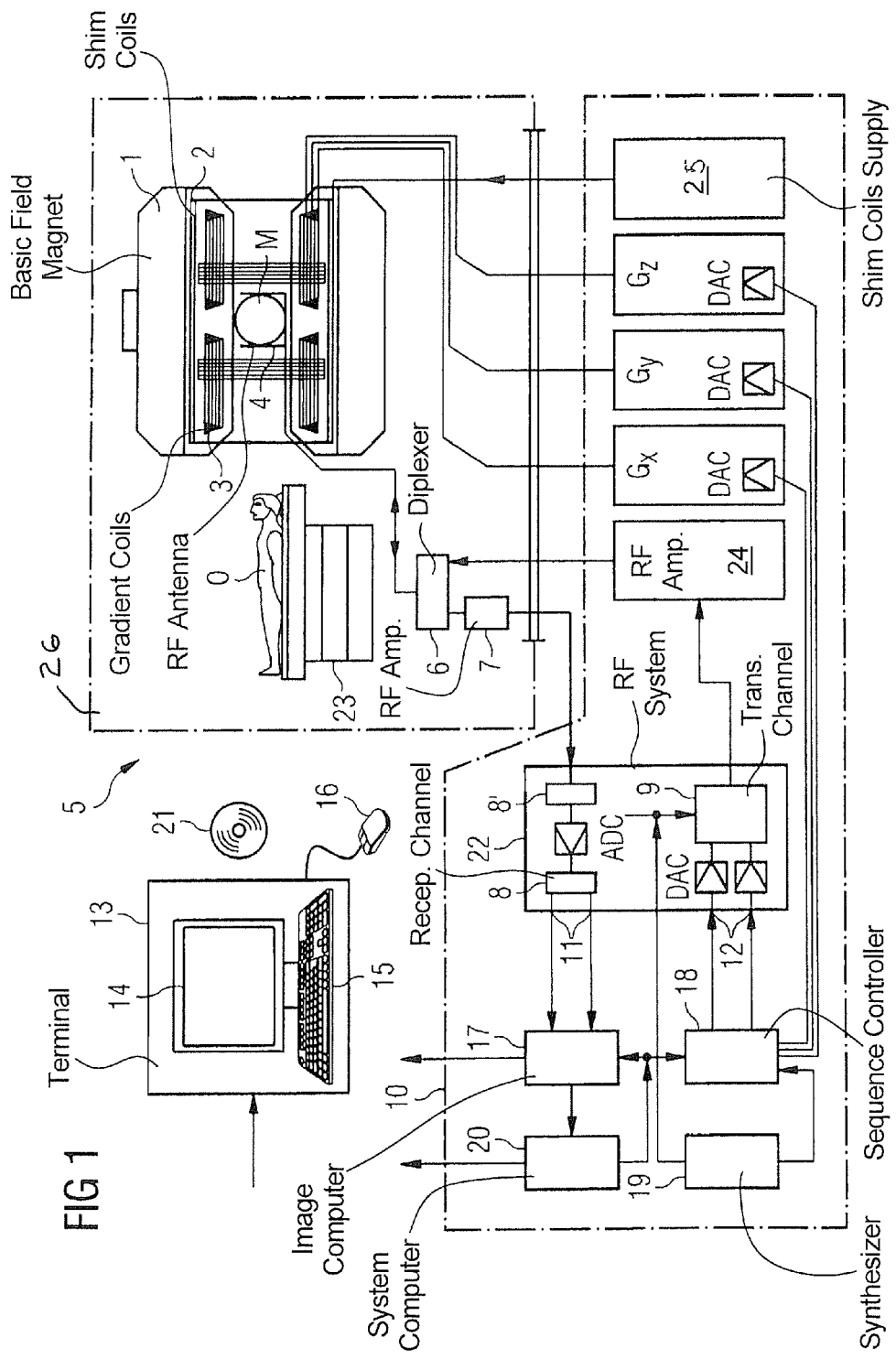
FIG. 1 schematically illustrates a magnetic resonance system according to the invention.

FIG. 1 is a schematic representation of a magnetic resonance system 5 (a magnetic resonance imaging or magnetic resonance tomography apparatus). A basic field magnet 1 generates a temporally constant, strong magnetic field for polarization or alignment of the nuclear spins in an examination region of a subject O—for example a part of a human body (the heart, for example)—that is to be examined. The subject O, lying on a table 23, is moved into the magnetic resonance system 4 for data acquisition. The high homogeneity of the basic magnetic field that is required for the magnetic resonance measurement (data acquisition) is defined in a typically spherical measurement volume M. Shim plates made of ferromagnetic material are mounted at suitable locations to adjust the homogeneity requirements, in particular to eliminate (compensate) temporally invariable influences. Temporally variable influences are eliminated (compensated) by shim coils 2, operated by a shim coils supply 25.

A cylindrical gradient coil system 3 composed of three sub-windings is located in the basic field magnet 1. Each sub-winding is supplied with current by an amplifier to generate a linear (and temporally variable) gradient field in a respective direction of a Cartesian coordinate system. The first sub-winding of the gradient field system 3 generates a gradient $G_x$ in the x-direction; the second sub-winding generates a gradient $G_y$ in the y-direction; and the third sub-winding generates a gradient $G_z$ in the z-direction. Each amplifier includes a digital/analog converter that is activated by a sequence controller 18 for appropriately timed generation of gradient pulses.

One (or more) radio-frequency antennas 4 that convert the radio-frequency pulses emitted by a radio-frequency power amplifier 24 into an alternating magnetic field for excitation of the nuclei and flipping of the nuclear spins of the subject O to be examined, or of the region of the subject O that is to be examined, are located within the gradient field system 3. Each radio-frequency antenna 4 is composed of one or more RF transmission coils and one or more RF reception coils in the form of an annular, advantageously linear or matrix-like arrangement of component coils. The alternating field emanating from the precessing nuclear spins—i.e. normally the nuclear spin echo signals caused by a pulse sequence composed of one or more radio-frequency pulses and one or more gradient pulses—is also converted by the RF reception coils of the respective radio-frequency antenna 4 into a voltage (measurement signal) that is supplied via an amplifier 7 to a radio-frequency reception channel 8 of a radio-frequency system 22. The radio-frequency system 22 furthermore includes a transmission channel 9 in which the radio-frequency pulses are generated for the excitation of nuclear magnetic resonance. The respective radio-frequency pulses are digitally represented in the sequence controller 18 as a series of complex numbers based on a pulse sequence predetermined by the system computer 20. This number sequence is supplied as a real part and imaginary part to a digital/analog converter in the radio-frequency system 22 via respective inputs 12, and from the digital/analog converter to a transmission channel 9. In the transmission channel 9, the pulse sequences are modulated on a radio-frequency carrier signal whose base frequency corresponds to the resonance frequency of the nuclear spins in the measurement volume.

The switching from transmission operation to reception operation takes place via a transmission/reception diplexer 6. The RF transmission coils of the radio-frequency antenna(s) 4 radiate(s) the radio-frequency pulses for excitation of the nuclear spins into the measurement volume M and receives the resulting echo signals via the RF reception coil(s). The correspondingly acquired magnetic resonance signals are phase-sensitively demodulated at an intermediate frequency in a first demodulator 8' in the reception channel (first demodulator) of the radio-frequency system 22 and digitized in an analog/digital converter (ADC). This signal is further demodulated at a frequency of 0. The demodulation at a frequency of 0 and the separation into real part and imaginary part occurs in a second demodulator 8 after the digitization in the digital domain. An MR image is reconstructed by the image computer 17 from the measurement data acquired in such a manner. The administration of the measurement data, the image data and the control programs takes place via the system computer 20. Based on a specification with control programs, the sequence controller 18 monitors the generation of the respective desired pulse sequences and the corresponding scanning of k-space. In particular, the sequence controller 18 controls the timed switching of the gradients, the emission of the radio-frequency pulses with defined phase amplitude and the reception of the nuclear magnetic resonance signals. The time base for the radio-frequency system 22 and the sequence controller 18 is provided by a synthesizer 19. The selection of corresponding control programs to generate an MR image (which control programs are stored on a DVD 21, for example) and the presentation of the generated MR image take place via a terminal 13 that includes a keyboard 15, a mouse 16 and a monitor 14.

The hardware components encompassed by the outline 10 constitute a control computer of the magnetic resonance system 5, and the components encompassed by outline 24 are commonly known in the art as a magnetic resonance scanner.

Figure 2:
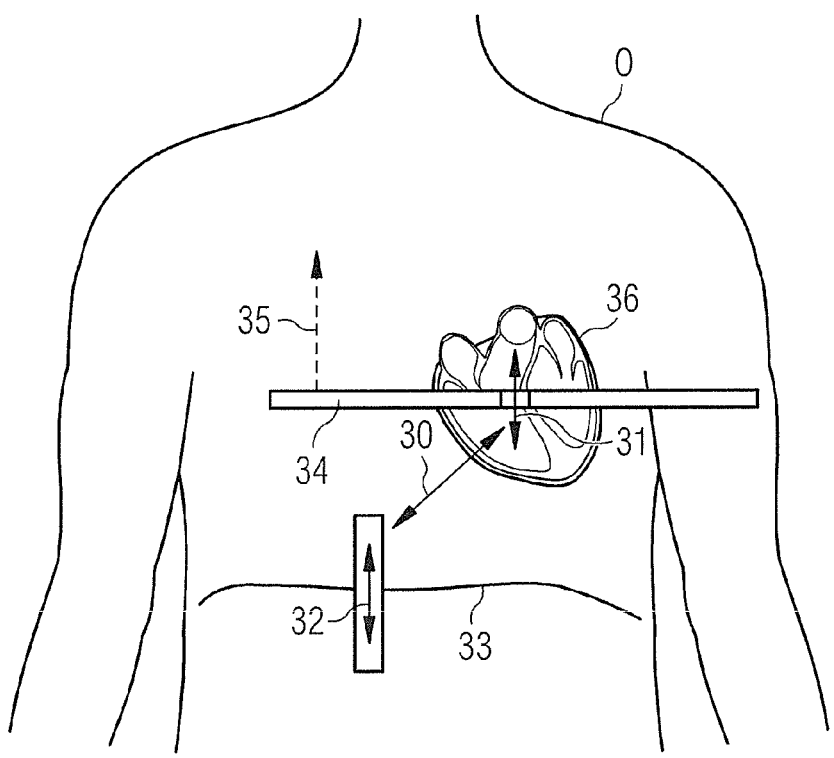
FIG. 2 schematically illustrates how MR data of the heart of an examination subject are acquired in accordance with the invention.

The manner by which the MR image data of the volume segment—in this case of the heart 36 of a patient O—are acquired is shown schematically as an example in FIG. 2. The MR data are acquired with a three-dimensional, segmented acquisition technique in which the entire heart region of interest is excited with an RF pulse. However, it is also possible to acquire the MR data two-dimensionally, i.e. slice-by-slice 34.

The heart or the coronary region of the heart 36 moves during the data acquisition, as is indicated by the double arrow 31. This movement or position change of a specified region within the heart 36 corresponds with the movement of the diaphragm 33, and the movement or position change of the diaphragm 33 is represented by the double arrow 32. The movement of the diaphragm 33 is also called breathing movement. The tracking factor 30 now defines a correlation between the movement of a specific region in the heart 36 and the movement of the diaphragm 33. In addition to being dependent on the respective coronary region, the tracking factor 30 is also dependent on the Z-coordinate along the Z-direction 35, which corresponds to the direction of the basic magnetic field of the magnetic resonance system (thus on the Z-position within the coronary region).

The flow chart of a method according to the invention is shown in FIG. 3.

In the first Step S1, within the scope of a pre-measurement tracking factors are determined for multiple coronary regions of the heart 36. Each coronary region is subdivided into multiple regions which lie atop one another in the Z-direction 35 such that these regions can be differentiated with regard to their Z-position. An individual tracking factor is determined for each of these regions.

MR image data of the predetermined volume segment (i.e. of the heart 36 and its environment) are acquired in the following Step S2. With the use of the navigator, the position of the diaphragm is acquired simultaneously with the acquisition of the MR image data at the point in time at which the MR image data are acquired. The acquired MR image data are stored together with the position of the diaphragm.

According to the presented method, the following program loop is implemented for each coronary region.

In Step S3, the position of the diaphragm is calculated for each region within the respective coronary region, depending on the tracking factor and the Z-position of the region. The Z-position of the respective region can be determined, for example, using a prominent point of the respective region.

The MR image data corresponding to the calculated position of the diaphragm are subsequently used to reconstruct the MR image data of the respective region in Step S4. The corresponding MR image data of a diaphragm position are at best those MR image data which have been acquired and stored for this diaphragm position in Step S2. If no MR image data have been acquired for a diaphragm position in Step S2, the MR image data corresponding to the diaphragm position are calculated from MR image data of at least one diaphragm position that is adjacent to the calculated diaphragm position.

If Steps S3 and S4 have been executed for all regions of the respective coronary region, the local reconstructions of the respective regions are combined into a complete MR image of the respective coronary region in Step S6.

In steps S7, it is determined whether an additional coronary region is present that has not been reconstructed. If so, the method loops back to S3. If a complete MR image for coronary regions is present, the MR image of the heart is created in that the MR images of all coronary regions are combined in Step S8. For example, this can be produced such that the respective coronary region is cut out of the complete MR image of the respective coronary region. The excised coronary regions are then assembled again in the MR image of all coronary regions.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to generate a magnetic resonance (MR) image of a predetermined volume segment of a living subject, comprising:
    operating an MR scanner to acquire MR data from a predetermined volume segment of a living subject, for different positions of a moving area of the living subject, said volume segment comprising a plurality of different regions within said volume segment;
    providing said MR data to a computer, and using said computer to determine the different position of the moving area and a respective tracking factor for each of said plurality of different regions of the volume segment that correlates movement of each different region to said moving area;
    for each of said different regions, using said computer to calculate a position of the respective region dependent on the position of the respective region and the tracking factor for the respective region, by determining the position of the respective region from the tracking factor dependent on a position of the moving area; and
    using the MR data and the calculated positions of the respective regions to reconstruct a motion-corrected image of each respective region wherein the calculated positions of the respective regions correct for motion of the respective regions due to said moving area, and making the reconstructed motion-corrected images available in electronic form from the computer as a data file.

2. A method as claimed in claim 1 wherein the living subject is a mammal and wherein the moving area is a diaphragm of the mammal.

3. A method as claimed in claim 1 wherein the living subject is a mammal, and wherein said predetermined volume segment comprises at least a portion of a region of the heart of the mammal, including an immediate environment of the heart of the mammal.

4. A method as claimed in claim 3 wherein said predetermined volume segment comprises a coronary region of the mammal.

5. A method as claimed in claim 1 wherein the living subject is a mammal and wherein the moving area is a diaphragm of the mammal and wherein the predetermined volume segment is at least a portion of a region of the heart of the mammal, including an immediate environment of the heart of the mammal.

6. A method as claimed in claim 5 wherein said regions of the volume segment are located at least partially atop one another in a direction of a basic magnetic field of the MR scanner, and wherein the position of the respective regions corresponds to a position along the direction of the basic magnetic field.

7. A method as claimed in claim 1 comprising acquiring said MR data of said volume segment for different positions of the moving area by a step-by-step automatic entry by said computer of said data unto an electronic memory organized as k-space that corresponds to a volume that comprises the predetermined volume segment, independent of the position of the moving area, and for each step in entering the MR data into k-space, acquiring only MR data of a partial segment of k-space for the corresponding position of the moving area, with MR data for each partial segment of k-space for the different positions of the moving area being acquired upon completion of said step-by-step entry of the MR data into k-space.

8. A method as claimed in claim 7 comprising for at least one of said partial segments of k-space, calculating data entered therein from a partial segment that is as close as possible to said at least one of said partial segments, and said position of said moving area, instead of entering MR data therein that are acquired from the volume segment.

9. A method as claimed in claim 7 comprising, for any of said partial segments of k-space for which MR data are not acquired, reconstructing missing MR data for said partial segments of k-space for which MR data are not acquired, by compressed sensing.

10. A method as claimed in claim 7 comprising identifying predetermined positions of said moving area and concluding acquisition of the MR data of the volume segment for different positions of the moving area only when all of said partial segments of k-space have been acquired for each predetermined position of the moving area.

11. A magnetic resonance (MR) apparatus comprising:
an MR scanner adapted to receive a living subject therein, said living subject comprising a moving area within the living subject;
a control computer configured to operate said MR scanner to acquire MR data from a predetermined volume segment of a living subject, for different positions of a moving area of the living subject, said volume segment comprising a plurality of different regions within said volume segment;
said control computer being configured to determine the different position of the moving area and a respective tracking factor for each of said plurality of different regions of the volume segment that correlates movement of each different region to said moving area;
said control computer being configured to calculate, for each of said different regions, a position of the respective region dependent on the position of the respective region and the tracking factor for the respective region, by determining the position of the respective region from the tracking factor dependent on a position of the moving area; and
said control computer being configured to use the MR data and the calculated positions of the respective regions to reconstruct a motion-corrected image of each respective region wherein the calculated positions of the respective regions correct for motion of the respective regions due to said moving area, and to make the reconstructed motion-corrected images available in electronic form from the control computer as a data file.

12. A non-transitory, computer-readable data storage medium encoded with programming instructions, said storage medium being loaded into a control computer of a magnetic resonance (MR) apparatus that comprises an MR scanner, said programming instructions causing said control computer to:
operate said MR scanner to acquire MR data from a predetermined volume segment of a living subject, for different positions of a moving area of the living subject, said volume segment comprising a plurality of different regions within said volume segment;
determine the different position of the moving area and a respective tracking factor for each of said plurality of different regions of the volume segment that correlates movement of each different region to said moving area;
for each of said different regions, calculate a position of the respective region dependent on the position of the respective region and the tracking factor for the respective region, by determining the position of the respective region from the tracking factor dependent on a position of the moving area; and
use the MR data and the calculated positions of the respective regions to reconstruct a motion-corrected image of each respective region wherein the calculated positions of the respective regions correct for motion of the respective regions due to said moving area, and make the reconstructed motion-corrected images available in electronic form from the control computer as a data file.

* * * * *